United States Patent [19]

Moore

[11] Patent Number: 4,961,147
[45] Date of Patent: Oct. 2, 1990

[54] APPARATUS FOR MEASURING THE ELECTRIC CHARGE CONDITION OF NON-CONDUCTIVE PARTICLES IN A LIQUID MEDIUM

[76] Inventor: Zack J. Moore, 519 Oak Dr., Lake Jackson, Tex. 77566

[21] Appl. No.: 413,635

[22] Filed: Sep. 28, 1989

[51] Int. Cl.$^5$ ............................................. G01N 27/60
[52] U.S. Cl. .................................... 324/446; 324/71.1; 324/453
[58] Field of Search ......................... 324/761, 46, 453; 210/746, 96.1

[56] References Cited

U.S. PATENT DOCUMENTS

| | | | |
|---|---|---|---|
| 3,365,376 | 1/1968 | Weyland | 324/447 |
| 3,368,144 | 2/1968 | Gerdes | 324/71.1 |
| 3,368,145 | 2/1968 | Gerdes | 324/71.1 |
| 3,369,984 | 2/1968 | Gerdes et al. | 324/71.1 |
| 3,526,827 | 9/1970 | Cardwell | 324/453 |
| 3,917,451 | 11/1975 | Graves et al. | 324/71.1 |
| 4,297,640 | 10/1981 | Moore | 324/458 |
| 4,446,435 | 5/1984 | Canzoneri | 324/71.1 |
| 4,820,990 | 4/1989 | Moore | 324/453 |
| 4,825,169 | 4/1989 | Carver | 324/71.1 |

FOREIGN PATENT DOCUMENTS

| | | | |
|---|---|---|---|
| 591050 | 10/1978 | U.S.S.R. | 324/453 |

Primary Examiner—Reinhard J. Eisenzopf
Assistant Examiner—Maura K. Regan
Attorney, Agent, or Firm—John Lezdey

[57] ABSTRACT

An apparatus for measuring the electrical charge condition of non-conductive particles in a liquid medium comprising a flow path having sensory means for developing a signal proportional to a desired ion activity and a reciprocating piston carrying a grounded electrode. The reciprocating piston induces liquid to flow past the sensory means and the electrode on the piston screens external galvanic interferences and lower electrode impedance. The electrical signals are monitored by an electronic component.

6 Claims, 2 Drawing Sheets

APPARATUS FOR MEASURING THE ELECTRIC CHARGE CONDITION OF NON-CONDUCTIVE PARTICLES IN A LIQUID MEDIUM

FIELD OF THE INVENTION

The present invention relates to a means for measuring the effects of the electrical double layer phenomena in heterogeneous electrochemical equilibria.

More particularly, the invention is concerned with an apparatus which is useful in obtaining quantitative information on the effects of the electrical double layer in a heterogeneous electrochemical system, for example the streaming potential and/or streaming current which is provided with a reciprocating electrode.

BACKGROUND OF THE INVENTION

The specific absorption of ions readily occurs at the interface between a non-conductive solid and an electrolyte solution. The exposed surface of any solid is covered with absorbed ions which define the limits of the inner Helmholtz plane. The accumulative charge making up this plane may be stoichiometrically compensated by an excess of oppositely charged ions diffusely dispersed throughout the bulk of a joining liquid phase in a direction perpendicular to the exposed solid surface. Ions of the opposite charge to those surface adsorbed can approach no closer than the outer Helmholtz plane. The space charge in the region between the outer immobile Helmholtz plane and the contacting mobile electrolyte gives rise to an electrokinetic driving force (defined as zeta potential) which plays an important role in explaining the equilibrium behavior of heterogeneous liquid-liquid or liquid-solid systems in industrial and civic processes such as flocculation control, water purification, waste management, etc. The influence of this electrical double layer upon equilibrium has been recognized for many years, however, any practical application of the concept has been seriously hampered by the absence of a suitable means of measurement.

It is conventional practice in clarifying aqueous systems containing suspended particles to employ a flocculation process. Once flocculated, the suspended particles can be separated from their fluid medium by sedimentation, filtration, floatation, centrifugation or one or more of the foregoing physical separatory processes in combination. Conventionally, the flocculation process is promoted by the use of flocculating chemicals such as alum, ferric chloride or various polymeric materials such as water-soluble cationic and anionic organic polyelectrolytes. Aqueous suspensions of finely divided polymeric particles are encountered in a paper machine headbox within a paper manufacturing process operation and in many other contexts. In a typical flocculation process for flocculating aqueous suspensions of finely divided particles, a water-soluble cationic flocculating chemical is added to the solution. The finely divided particles suspended in the solution are normally negatively charged and thus, the addition of the cationic agent results in charge neutralization on the suspended particles. When the average charge is zero, or some other predetermined value, the dispersed organic and/or inorganic particles undergo flocculation, i.e., aggregation at an increased rate. Too much cationic agent, however, creates positively charged particles which can be as difficult to flocculate as are the originally negatively charged particles.

To date, however, determining how much chemical to add to the stream to be treated has been difficult, especially since the composition of such stream often varies over fairly wide ranges and time intervals of a few minutes to a few hours.

Various empirical approaches to "finding" the correct dosage of flocculate to be added to a stream have been used. For example, increasing amounts of flocculant may be added to samples from the stream and amount of decrease in turbidity of the stream noted, the correct dosage being determined as the one which causes the greatest decrease in turbidity with the least addition of flocculant. Such a procedure is time consuming and therefore not really suitable where the composition of the treated solution varies, since the information resulting from this procedure is no longer valid or applicable since the treated solution will have varied by the time the data has been corrected.

Another approach is to use a so-called Zeta meter to determine zeta-related electrokinetic phenomena such as the charge condition existing in the stream. The Zeta meter is used to observe the time required for a single charge particle from the stream to pass a predetermined distance along a liquid path while under the influence of an electric field at a given temperature. The method is time consuming and requires a technician to perform the test and to interpret test results before the stream is treated with greater, lesser, or the same amount of flocculant as had been used since the last previous Zeta meter test was made.

U.S. Pat. No. 3,368,145 to W. F. Gerdes discloses an apparatus which provides a continuous measurement of the charge density of the absorbed material taken from the process stream.

U.S. Pat. No. 4,297,640 to Z. J. Moore which is herein incorporated by reference discloses an apparatus for measuring the electric charge of non-conductive particles in a mildly conductive electrolyte which incorporates a grounded stationary electrode in a special location with respect to two sensing electrodes. The guard electrode while effective does not completely eliminate all potential galvanic interferences.

U.S. Pat. No. 4,446,435 to Canzoneri discloses an ultrasonic streaming current detector for developing on a continuous basis, an electrical signal which is a function of the charge condition existing in a stream containing charged particles.

U.S. Pat. No. 4,449,101 to Canzoneri et al relates to a jet wash apparatus for an ultrasonic streaming current detector with means for variably conveying a cleaning fluid into the detector.

U.S. Pat. No. 4,820,990 to Z. J. Moore relates to an electrodeless apparatus for determining a function of an electrical charge condition utilizing an electrostatic or inductive coupling. The apparatus has limited utility since it is essentially for use in pure liquid systems.

SUMMARY OF THE INVENTION

In accordance with the present invention there is provided a means for obtaining a quantitative measure of electrokinetic properties in a two phase liquid-liquid or liquid-solid system wherein said means contains an electrically non-conductive inert barrier which separates the measured fluid from the measuring circuitry.

More particularly, the invention relates to an apparatus for determining a function of the electrical charge condition in a flowable liquid media containing electrical charge influencing species, particularly electrical charge influencing species which are electrically non-conductive themselves but on whose surface electrical charges collect.

It has now been found that a very stable, long-life accurate apparatus for measuring a streaming current and/or streaming potential of charged non-conductive particles suspended in a mildly conductive electrolyte can be synergistically achieved with the addition of a grounded reciprocating electrode to an apparatus similar to that which is disclosed in U.S. Pat. No. 3,368,145. That is such an improved apparatus can be achieved if a grounded reciprocating electrode is located in proper relationship to the two sensing electrodes and the remainder of the apparatus.

More specifically, the improved apparatus is useful in determining the electrical charge condition in a flowable liquid media containing a mildly conductive liquid electrolyte and electrical charge influencing species, particularly electrical charge influencing species which are electrically non-conductive themselves but on whose surfaces electrical charges collect. From U.S. Pat. No. 3,368,145, the conventional parts of this apparatus are known to comprise a flow path member, or cylinder, open at one end and having electrically insulating walls. A pair of spaced, sensing electrodes is provided with one of the electrodes being near the closed end of said flow member and the other being near the open end of said flow path member. A reciprocating member is provided with a grounded electrode located on said reciprocating member at least partially within the tubular flow path member. The reciprocating member causes liquid to flow to and fro in the flow path member in a repetitive manner. Such reciprocating member can be a piston loosely fitted and slidably mounted in said flow path member. Means are taught as being coupled to said electrodes for amplifying and utilizing and electrical signal induced across said electrodes. The flow path member is disposed so that a continuously different sample of the flowable liquid media can be passed in and out of the cylinder in the space between the walls of the tubular flow path member and the walls of the reciprocating member past the sensing electrodes.

The improvement of the present invention is the addition of a grounded electrode in the tubular flow path on the reciprocating member.

This grounded electrode is grounded and preferably has a substantially larger surface area than the two sensing electrodes.

The reciprocating electrode yields a self-cleaning process.

By the present arrangement, the ground electrode can go to the top of the fluid whereby the electrode resistance to the solution is lowered by the increased surface area. Consequently, the lowered electrode impedance makes the apparatus more effective in screening galvanic interference than the apparatus of U.S. Pat. No. 4,297,640.

These and other features of the present invention may be more clearly observed by reference to the drawing and detailed description of the preferred embodiment of the present invention.

DESCRIPTION OF THE PREFERRED EMBODIMENTS

Figure 1:
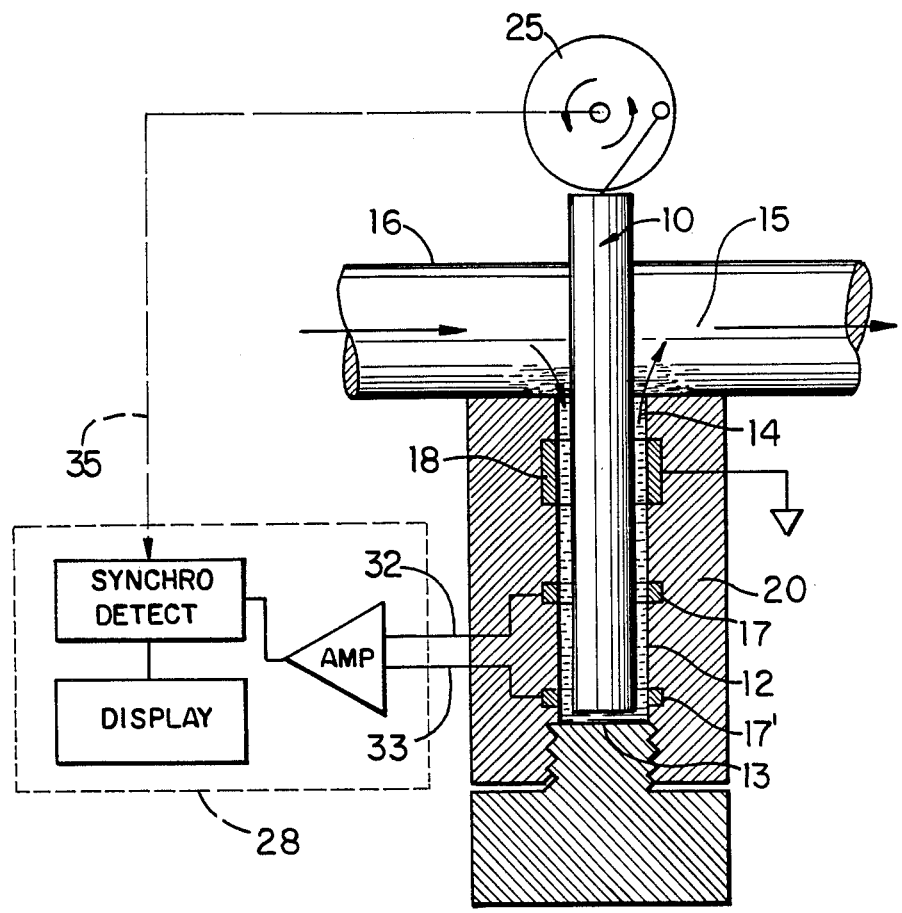
FIG. 1 is a partially diagrammatic sectional elevation of a prior art apparatus.

Although specific terms are used in the following description for the sake of clarity, these terms are intended to refer only to the particular structure of the invention selected for illustration in the drawings, and are not intended to define or limit the scope of the invention.

Referring to FIG. 1 of the drawing, there is shown an apparatus of the type disclosed in the aforementioned U.S. Pat. No. 4,297,640, which is incorporated herein by reference. The apparatus comprises an electrically inert flow path member or cylinder 12, open at its upper end 14 and closed at the bottom end 13. The upper end 14 is exposed to a flowing liquid stream 15 containing a conductive electrolyte and electrical charge influencing species which are electrically non-conducting.

A non-conductive reciprocating member or piston 10 is located within the flow path member or cylinder 12 to cause liquid therein to flow into and out of the small opening opening 14 in a repetitive manner. The piston 10 may be loosely fitted and slidably mounted in the flow path member.

The piston 10 is supported and reciprocated by means of a mechanical drive package such as electric motor driven cam 25. Advantageously, the piston 10 is reciprocated at a slow frequency, for example about four cycles per second. Fluids enter the opening at the upper end on the upstroke of the piston 10 and are expelled on the down stroke. The fluids are totally contained by the piping 16 and the cylinder 12.

The entire cylinder 12 is composed of galvanically non-conductive material to form a low dielectric barrier to prevent exposure of the non-electrode portion of the measuring apparatus.

There is provided a grounded guard electrode 18 and two sleeve conductors 17, 17' which are inset in the wall of the support cylinder 12. The conductors 17, 17' are separated from each other at a distance to provide optimum signal response based on the chosen cylinder length and piston stroke length. The conductors 17, 17' are electrically connected to signal processor 28 by lead lines 32, 33 so that signals caused to be produced in the conductors 17, 17' by the action of the reciprocating piston 10 can be simultaneously processed.

All of the stationary components of the measurement cell are stabilized by a low dielectric, low conductivity inert plastic support medium 20. A signal proportional to the desired ion activity is thus developed across the non-conductive inert cylinder wall.

Figure 2:
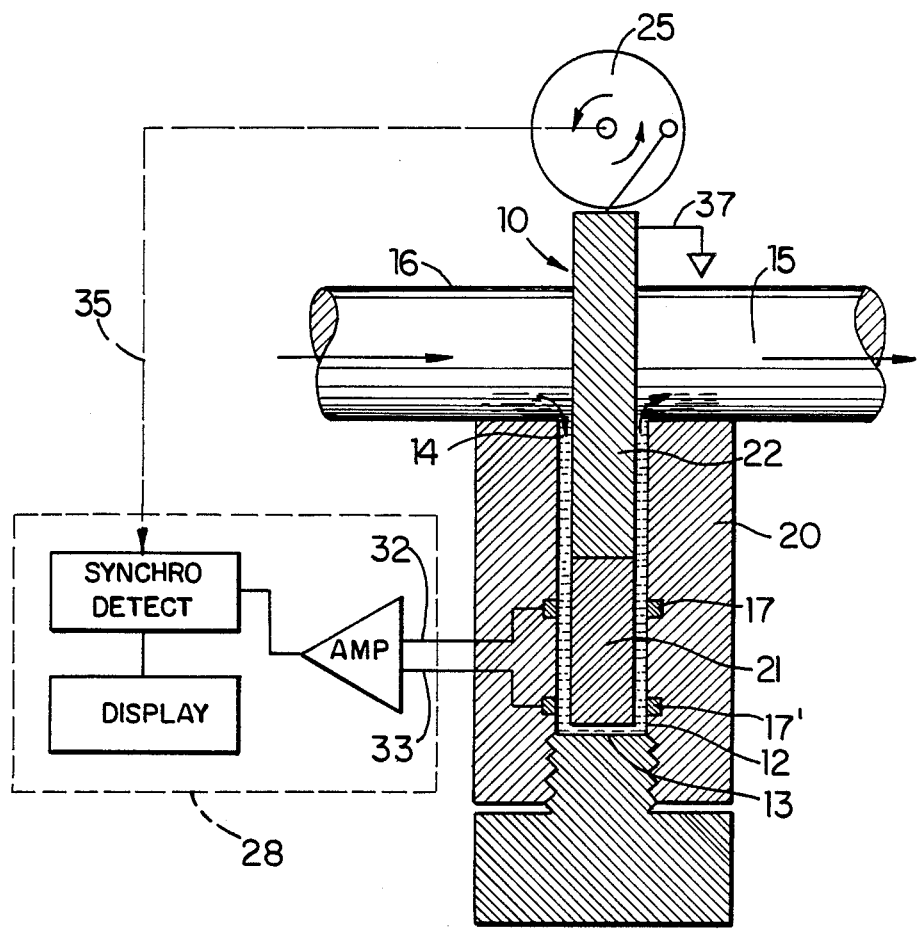
FIG. 2 is a partially diagrammatic sectional elevation of an apparatus of the invention.

FIG. 2 illustrates an apparatus of the invention wherein inside of cylinder 12 are located two electrodes 17 and 17'. These electrodes 17 and 17' are inset in the wall of the cylinder 12. These electrodes are thin cylindrical rings fitting around the wall of cylinder 12. Electrodes 17 and 17' are the sensing electrodes and have wire leads 32 and 33 leading through a pipe section 16. Leads 32 and 33 exit from pipe section 16 inside a single, shielded cable (not shown) to prevent stray electrical interferences from altering the very small electrical signals transmitted from the sensing electrodes 17 and 17' through leads 32 and 33.

Electrodes 17 and 17' are arranged as shown, i.e., one electrode 17' is located near the bottom of cylinder 12 and another 17 is spaced toward the top and electrode 22 is located near the top of the cylinder. The reciprocating member or piston 10 carries an electrode 22 and an inert portion 21 at its lower part. The electrode 22 is connected to a ground 37. The electrode 22 presents a large surface area and extends into the flow path 16 of the liquid 15 to screen galvanic interferences.

OPERATION OF THE APPARATUS

The operation of the apparatus of the invention is as follows. Mildly conductive liquid containing non-conductive particles, the electric charge conditions of which is desired to be continuously monitored, is flowed through pipe 16 from an external pipe. Piston 10 is reciprocated at about four cycles per second by an electric motor driven cam 25 in mechanical drive system. As the liquid flows over the top of cylinder 12 it is forced in and out of cylinder 12 by the combined action of gravity and hydraulic forces caused by the reciprocating piston 10. Liquid from this flow is forced at a relative high pressure and velocity in and out of the small open annulus located between piston 10 and cylinder 12. Hence, this liquid necessarily flows past reciprocating electrode 22 and the sensing electrodes 17 and 17'. This flow causes what is referred to as a streaming potential to exist between the sensing electrodes and a streaming current to flow between the sensing electrodes 17 and 17' and through electrical lead lines 32 and 33. This streaming potential and streaming current are electrical in nature and are a function of the electrical charge on the non-conductive particles in the liquid. The streaming current and potential are proportional to this electric charge condition and alternate at the same frequency as the reciprocating frequency of piston 10. The electrode 22 in the flow path screens galvanic interferences originating from external sources.

Electronic package 28 processes the alternating current (A.C.) electrical signals so that they become direct current (D.C.) signals which are a function of the desired electrical charge conditions of the liquid.

Electrical conduction lines 35 connect mechanical component 25 to electrical component 28 so that the A.C. signals caused to be produced in lines 32 and 33 by the reciprocating piston driven by the mechanical drive can be synchronously demodulated to D.C. electrical signals by the electronics component 28. Advantageously, the reciprocating motions of the piston results in a wiping action which maintains a clean electrode surface for electrode 22. Also, the electrode on the piston extends beyond the sensing electrodes so as to yield a large surface area exposed to the process fluid to screen galvanic interferences and lower electrode impedance.

Preferably the lower piston portion, and/or plastic support compositions consist of any one or a combination of the following:
polyhalogenated polymers and copolymers;
polypseudohalogenated polymers and copolymers;
polyurethanes;
silica, oxides and hydrates;
silicates, nitrides, carbides, borates and borides;
metal oxides and hydrates;
resins including vinyl-ester resins;
polymeric hydrocarbons and the like.

The electrodes may comprise any suitable electrically conductive material, such as gold. Most preferable is silver, platinum, palladium, silver, etc.

Although the invention has been described with a certain degree of particularity, it is understood that the present disclosure has been made only by way of example and that numerous changes in the details of construction and the combination and arrangement of parts may be resorted to without departing from the spirit and scope of the invention.

What is claimed is:

1. An apparatus for sensing and quantifying the electrical charge condition in a flowable liquid media containing electrical charge influencing species comprising a flow path member, said flow path member having electrically insulating walls, an open end and a closed end, said flow path being so disposed that it may be substantially filled with said liquid, a reciprocating member carrying a grounded electrode disposed within said flow path member for mechanically inducing the ions in said liquid to flow in more than one direction, said reciprocating member having a transverse cross-sectional configuration such that said reciprocating member fits adjacent but spaced from said electrically insulating walls of said flow path member, means for admitting predetermined amounts of flowable material to said flow path member, sensory means in said flow path member for developing a signal proportional to a desired ion activity, and means coupled to said sensory means for amplifying any electrical signal induced across said sensory means.

2. The apparatus of claim 1, wherein said sensory means comprises two conductors.

3. The apparatus of claim 1, wherein said grounded electrode lowers electrode impedance and screens external galvanic interferences.

4. The apparatus of claim 1, wherein said sensory means and said electrode comprise silver.

5. The apparatus of claim 1, wherein said grounded electrode is self-cleaning.

6. An apparatus for sensing and quantifying electrical energy derived from zeta influenced ions in a flowable two phased liquid stream comprising:
an electrically insulated flow path member having an open end and a closed end, said flow path member being disposed so as to be filled substantially with said liquid stream;
an electrically insulated reciprocating member disposed within said flow path, said reciprocating member comprising an upper portion which is a grounded electrode and a lower inert portion, said grounded electrode screening external galvanic interferences, said reciprocating member causing the liquid, stream in said flow path to flow in more than one direction and exciting ions in said liquid;
a pair of spaced electrodes encircling said flow path and in contact with said liquid stream for sensing said mechanically induced excited ions in said liquid, said spaced electrodes developing a signal proportional to said mechanically induced ion activity; and
means for amplifying the electrical signals induced across said spaced electrodes.

* * * * *